(12) United States Patent
Wohlfarth

(10) Patent No.: US 7,990,141 B2
(45) Date of Patent: Aug. 2, 2011

(54) STREAMLINED DIAGNOSTIC MR IMAGING REQUIRING ONLY THREE CONTROL PARAMETERS OF OPERATOR SELECTED BOUNDARY CONDITIONS

(75) Inventor: Katrin Wohlfarth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/551,872

(22) Filed: Sep. 1, 2009

(65) Prior Publication Data

US 2010/0052680 A1    Mar. 4, 2010

(30) Foreign Application Priority Data

Sep. 1, 2008 (DE) .................. 10 2008 045 277

(51) Int. Cl.
*G01V 3/00* (2006.01)
(52) U.S. Cl. .................... 324/307; 324/309; 324/318
(58) Field of Classification Search .......... 324/300–322; 600/407–435; 382/128–131
See application file for complete search history.

(56) References Cited

U.S. PATENT DOCUMENTS

| | | | | |
|---|---|---|---|---|
| 6,512,373 | B1* | 1/2003 | Griffin et al. | 324/318 |
| 6,529,762 | B1 | 3/2003 | Ladebeck | 600/410 |
| 6,575,969 | B1* | 6/2003 | Rittman et al. | 606/41 |
| 6,687,527 | B1* | 2/2004 | Wu et al. | 600/410 |
| 6,801,037 | B1* | 10/2004 | Zhang | 324/309 |
| 7,081,750 | B1* | 7/2006 | Zhang | 324/309 |
| 7,443,166 | B2* | 10/2008 | Heid | 324/322 |
| 2002/0087066 | A1 | 7/2002 | Hellinger | 600/410 |
| 2008/0024129 | A1* | 1/2008 | Heid | 324/307 |
| 2010/0052680 | A1* | 3/2010 | Wohlfarth | 324/309 |

OTHER PUBLICATIONS

"Leitlinien der Bundesärztekammer zur Qualitätssicherung der Magnet-Resonanz-Tomographie," (1999).

* cited by examiner

*Primary Examiner* — Brij B. Shrivastav
*Assistant Examiner* — Tiffany A Fetzner
(74) *Attorney, Agent, or Firm* — Schiff Hardin LLP

(57) ABSTRACT

In a method for operation of a magnetic resonance system, at least one control device is fashioned for image data acquisition and corresponding components, and only three first control parameters defining primary boundary conditions are selected by an operator of the system, namely the contrast response, the spatial orientation of the at least one image data set to be acquired and the examination organ. Additional, second control parameters, required to control the components for image acquisition and defining secondary boundary conditions, are automatically determined by the control device using the first control parameters.

14 Claims, 3 Drawing Sheets

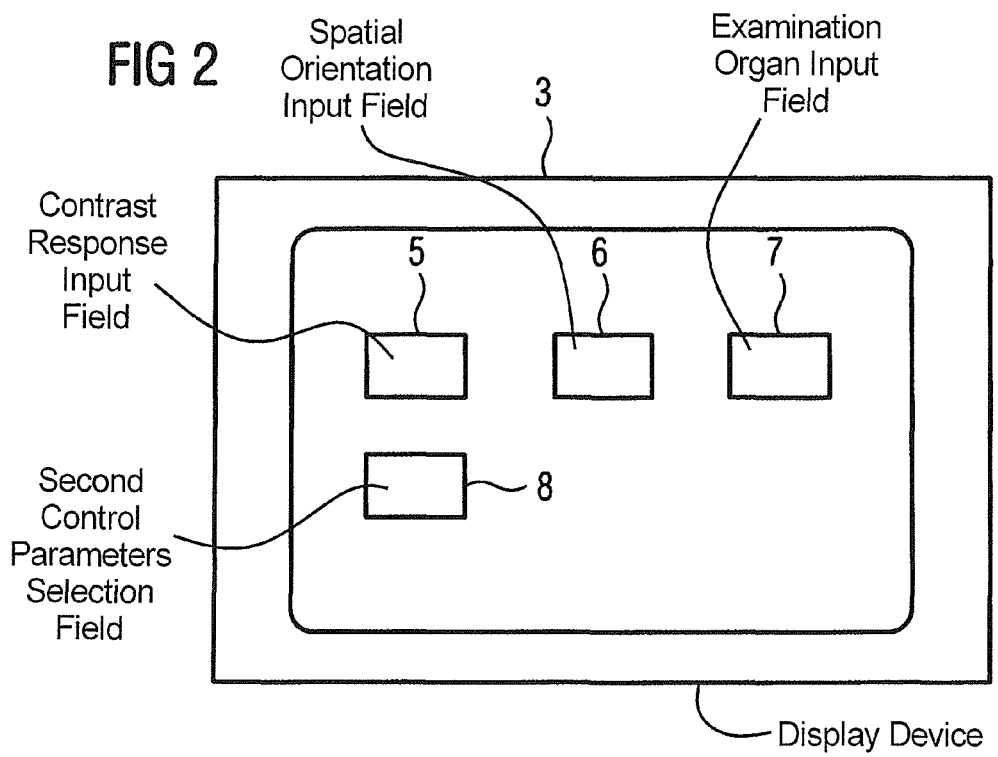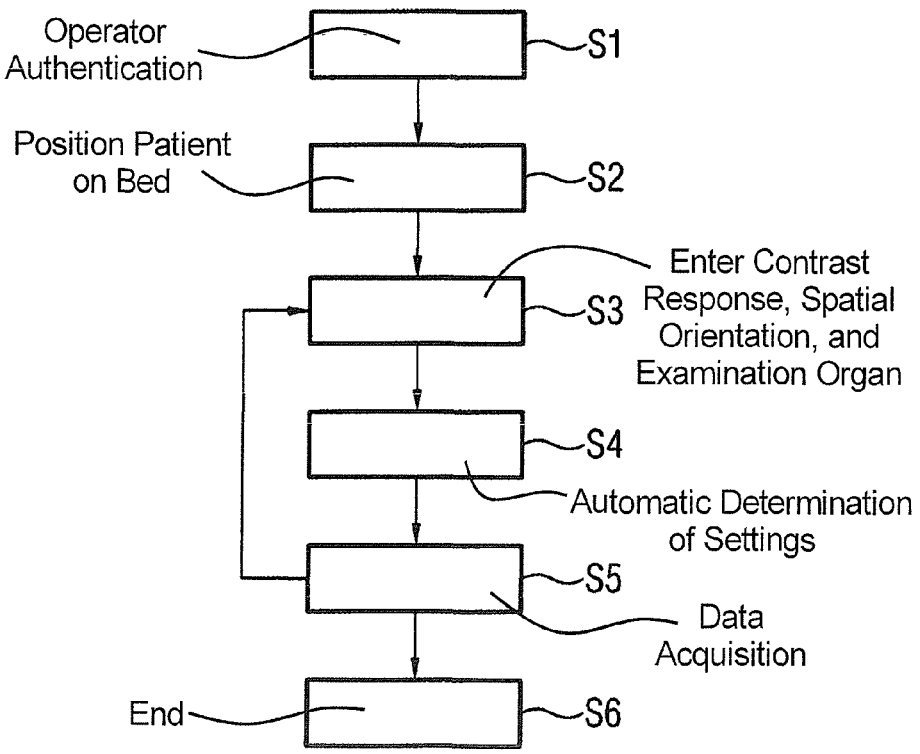

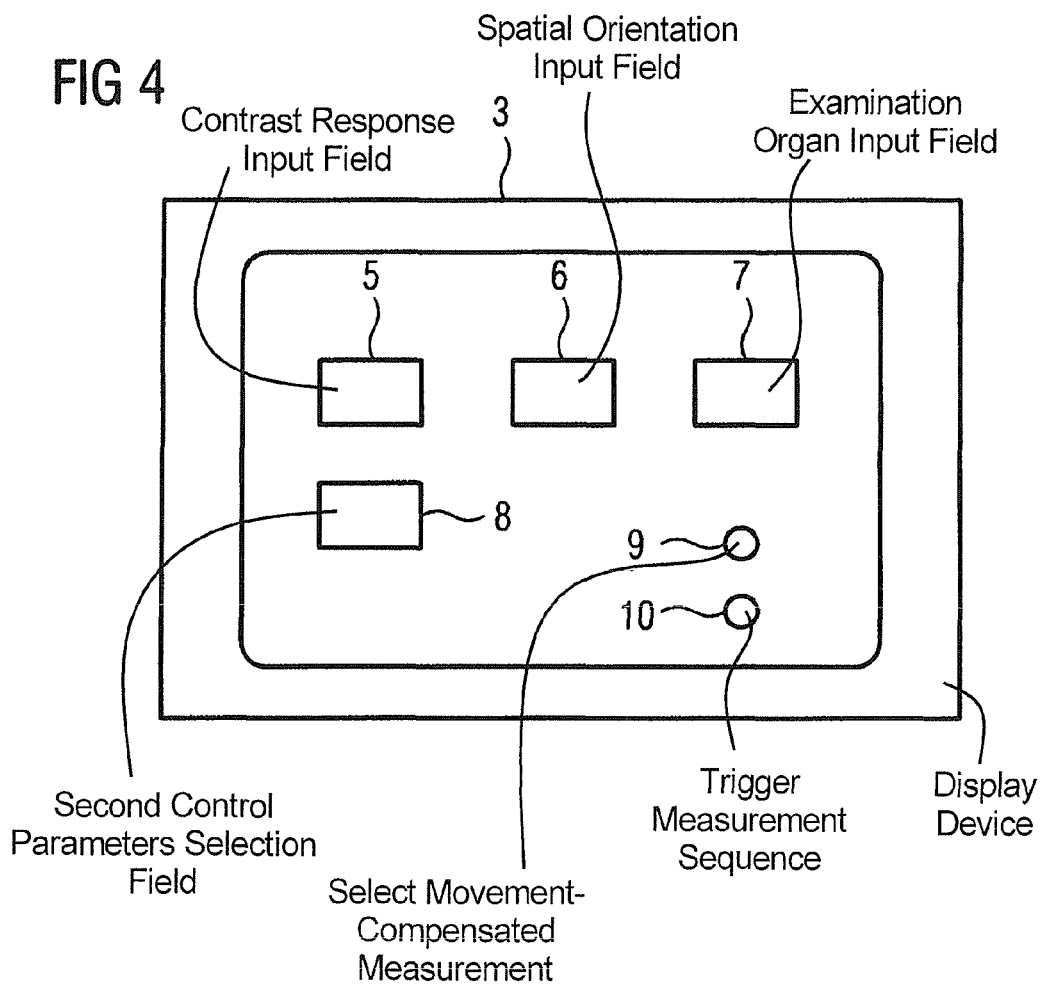

STREAMLINED DIAGNOSTIC MR IMAGING REQUIRING ONLY THREE CONTROL PARAMETERS OF OPERATOR SELECTED BOUNDARY CONDITIONS

BACKGROUND OF THE INVENTION

1. Field of the Invention

The present invention concerns a method to operate a magnetic resonance system of the type having at least one control device fashioned for image data acquisition, and corresponding components.

2. Description of the Prior Art

Computerized procedures known as measurement protocols are typically used to operate a magnetic resonance system. In addition to the measurement sequence defining the temporal arrangement of radio-frequency pulses, magnetic field gradients and acquisition points in time, are all relevant control parameters which are defined in these measurement protocols. When the system operator loads such a protocol, he or she can begin the measurement (i.e. the diagnostic imaging) data acquisition with the preset control parameters; otherwise the operator is forced to set the control parameters more or less by hand.

The control parameters include parameters whose meaning can easily be determined, for instance the layer thickness. For other control parameters, however, the effects when changed by the operator are not readily apparent. The bandwidth of the radio-frequency pulses is an example of the latter case.

In every case, the possibility for improved adjustment of the data acquisition requires a significant degree of background knowledge.

It is also typical to store a single sequence (for example a FLASH sequence) with control parameters respectively modified for different purposes in various protocols. In addition to the sequence, a protocol thus also contains the specific control parameters, for instance the echo time or the repetition time. Differences in the use result, for example a triggering of the measurement data acquisition is generally required in measurements of the heart, but this triggering that can be suppressed in measurements in the abdomen or in the brain. In spite of the presence of a specific sequence in the memory device of the control device, the stored sequence is thus not optimized for all possible applications. It further complicates matters that a number of sequences are known in magnetic resonance tomography. For example, an expert in the field of measurements of the brain would normally not be able, without further measures to correctly set a measurement sequence for acquisition of the heart, (an "expert" being a person with background knowledge of the physics and data acquisition by means of magnetic resonance tomography). The generation of new protocols with existing sequences is accordingly even more complicated for physicians or medical technology employees. Problems also arise when apparatuses of different manufacturers are used. Normally no uniform names from manufacturer-to-manufacturer are provided for identical sequences, such that a user can have problems upon operation if he or she must operate with a new apparatus that is possibly unknown to the operator or is only rarely used.

Known methods for automation of the magnetic resonance measurements do not provide assistance in this regard. For example, it is known to automatically detect the position and orientation of a patient. It is also known to automatically evaluate measurement data in order to generate from these control parameters for the next data set to be acquired. However, this requires that this data set is already defined to the greatest possible extent. For example, if the precise position of an organ to be acquired is determined from an overview image, the control parameters to be set are basically apparent in the slice positioning, but all additional control parameters necessary for data acquisition must be known beforehand, or must be stored as a protocol.

SUMMARY OF THE INVENTION

An object of the present invention to provide a method for operation of a magnetic resonance system in which the creation of measurement protocols is significantly simplified.

This object is achieved in accordance with the invention by a method for operating a magnetic resonance system wherein only three first control parameters, defining primary boundary conditions, are selected by the user (operator), namely the contrast response, the spatial orientation of the at least one image data set to be acquired and the examination organ, and additional, second control parameters required to control the components for image acquisition, and defining secondary boundary conditions, are automatically determined by the control device using (dependent on) the first control parameters.

Only a minimum knowledge thus is required on the part of the user in order to be able to operate the magnetic resonance system. While the examination organ in and of itself requires no additional explanation, the spatial orientation is also very easy to understand.

$T_1$ and/or $T_2$ and/or diffusion and/or perfusion and/or magnetization transfer contrast and/or proton density and/or spin density weighting or quantification and/or fat saturation contrast can advantageously be used as a contrast response. A number of possibilities to weight the signal response of the tissue in the acquired data sets differently are known in the field of magnetic resonance tomography. For example, a long echo time in a gradient echo produces a $T_2^*$ weighting while a $T_2^*$ quantification is also possible via acquisition of multiple temporally offset echoes. For the most part, there are multiple methods in order to achieve images with a specific weighting or quantification. For example, for $T_1$ quantification it is known to sample the relaxing magnetization with a plurality of FLASH experiments after a 180° inversion pulse. Alternatively, a 90° pulse can also be used, followed by a dephasing gradient. After this saturation module the relaxing longitudinal magnetization is then read out with different wait times by means of a spin echo or even a RARE.

Apart from differences in the measurement duration, the individual sequences are also different to the extent that RARE-based sequences are problematic in magnetic resonance systems with field strengths greater than 1.5 Tesla due to problems of interaction between radiated radio-frequency energy and corresponding heating of the tissue. However, not only the corresponding problem with regard to the specific absorption rate is known to those skilled in the art, but also susceptibility differences at higher field strengths also produce more severe dephasing artifacts, for example, which is why the echo time is to be minimized given use of a gradient echo sequence.

According to the invention, a user thus no longer has to meddle with such detailed knowledge; he merely sets the desired contrast response.

The sagittal, the coronal or the transversal orientation can advantageously be used as an orientation. Double oblique or in-plane rotated orientations can also be used. Furthermore, "eye", "ear", "throat", "heart" or any other localizable body region can particularly advantageously be used as an examination organ. These settings are not to be viewed as entirely independent of one another since the orientation is also apparent with regard to the examination organ. If the transversal orientation is selected as a spatial orientation of the image data set to be acquired, the measurement plane divides the patient into top and bottom, so to speak. However, this orientation is relative to the patient and not desired with regard to the apparatus. Methods already exist in order to adapt the desired orientation to the position of the patient in the magnetic resonance system. From the user side it is therefore insufficient to specify the desired orientation.

The examination organ can also be automatically discovered by the magnetic resonance device as soon as it has been defined by the user. For this there are also already a number of methods that, for example, are based on an evaluation of positioning image data sets that can be created automatically.

The specification of the three first control parameters alone thus allows the user to acquire an arbitrary data set without outside help and with minimal knowledge. The second control parameters that are required to control the components of the magnetic resonance system can be determined solely from the or using the three first control parameters. For a $T_1$ weighting, for example, the repetition time in a spin echo sequence is to be selected comparably short, while in a gradient echo or FLASH either the flip angle is set to a relatively large value (for example from 15-30°) or the repetition time is likewise selected to be short, for example 10-20 ms. The measurement sequence that is to be used is therefore selected depending on the magnetic field strength $B_0$ of the basic field magnet and the examination organ. The contrast ratio for $T_1$ can be set via the repetition time or the flip angle; the $T_2$ weighting can be set via the selection of the echo time etc. In principle, for the contrasts it is known how corresponding sequence parameters are to be set in order to achieve the corresponding effect. The slice thickness, the number of slices to be acquired and the spatial resolution can then also be set depending on the examination organ.

The second control parameters can be set individually or in groups to defined values deviating from the value determined by the control device. It can thereby be ensured that basic specifications desired by the user can be taken into account. For example, these can be specifications of a clinic management that generally desires a specific resolution and a specific number of slices in acquisitions of the eye. This can even go so far that more or less all second control parameters are established in a defined combination depending on the first control parameters. Naturally, the second control parameters can also be modified by an experienced user insofar as the user possesses the corresponding authorization. The user should also in no way be restricted by these possibilities; rather, these should deal with already enabling an optimized data acquisition by means of a minimum required set of information. If the user would like to modify the control parameters based on his or her expertise or for experimentation, the user should not be precluded from doing so.

The first and second control parameters can be stored with regard to persons. The user of a magnetic resonance system typically must first authenticate himself or herself at the control device. In the course of a study, the same measurement protocols are typically always used, always with the same settings. Through a personalized storage of the control parameters and of the sequence of the protocols that are thereby defined, it is even possible to have a complete data acquisition of a patient run automatically. After the authentication, both the positioning of the patient and the additional data acquisition can then run fully automatically, so an optimized workflow is achieved. It is also possible for an experienced user to prepare a specific measurement workflow for a less experienced user, who only then needs to call this work-flow. The experienced user thus also profits from the use of the first control parameters according to the invention since, he or she can compose the measurement protocols with minimal time cost.

The invention additionally also concerns a magnetic resonance device configured to operate in accordance with the above-described method.

BRIEF DESCRIPTION OF THE DRAWINGS

FIG. 2 schematically illustrates a display device in the implementation of the inventive method.

FIG. 3 is a workflow diagram of an MR examination in accordance with the inventive method.

FIG. 4 shows an alternative embodiment of a display device.

DESCRIPTION OF THE PREFERRED EMBODIMENTS

Figure 1:
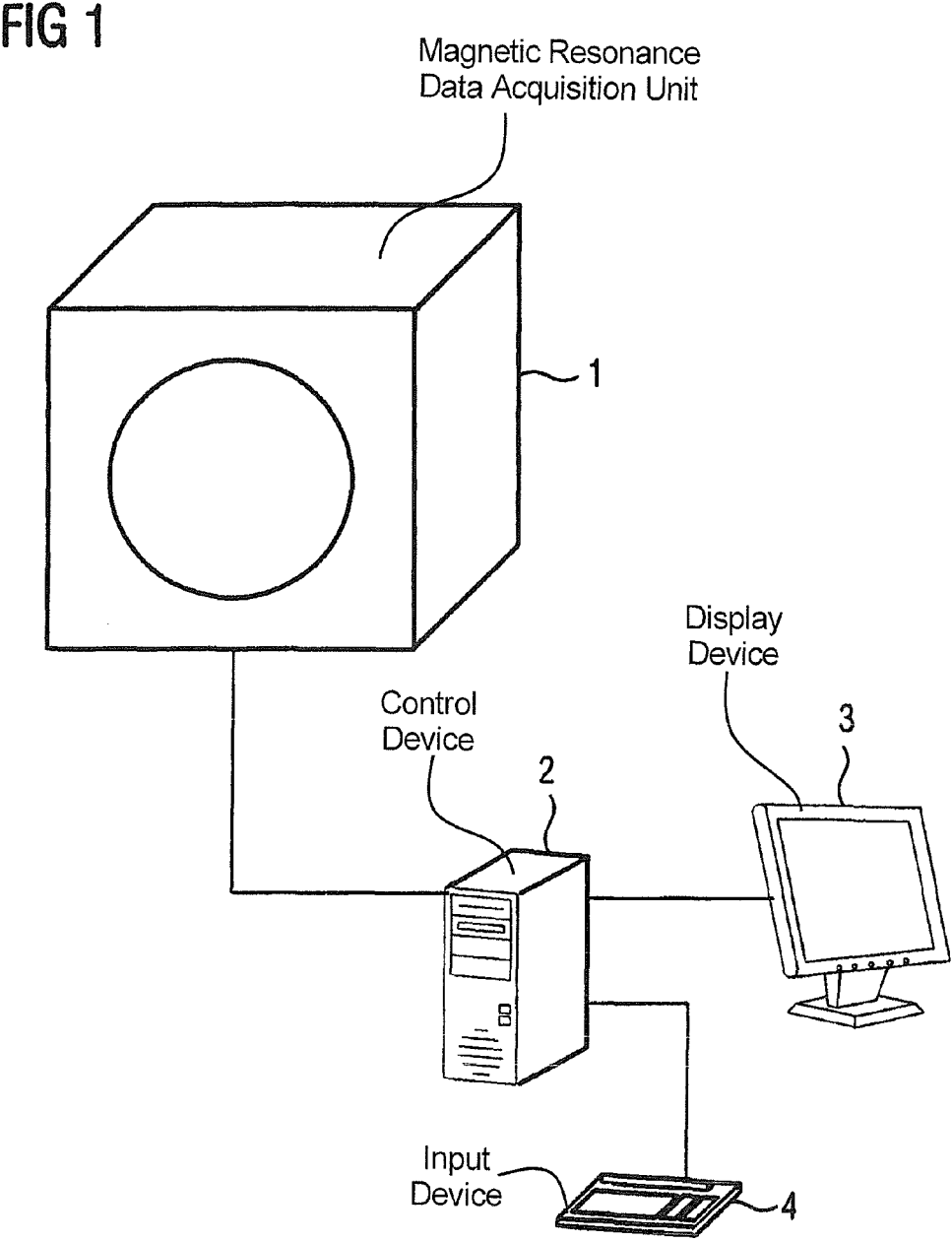
FIG. 1 schematically illustrates the basic components of a magnetic resonance system.

FIG. 1 shows a magnetic resonance data acquisition unit (scanner) 1 with a control device 2 and a display device 3 and an input device 4 associated with the control device 2. Details of the magnetic resonance system in the form of a radio-frequency coil and the like are well known to those skilled in the art and therefore need not be presented in detail herein.

FIG. 2 shows a basic representation of the display device 3 as it is presented to the user after authentication. The input field 7 is available for selection of the examination organ in addition to the input field 5 for the contrast response and the input field 6 for the spatial orientation. Furthermore, the selection field 8 with which the input fields for the second control parameters can be opened is available for experienced users.

The workflow for measurement data acquisition on a patient is hereby significantly simplified, as is apparent in FIG. 3. In a first Step S1, the operator authenticates himself or herself at the control unit 2 via the input device 4. The patient is subsequently positioned on the patient bed in Step S2. This merely means that the patient is instructed to take a position on the patient bed of the magnetic resonance system 1 that is advantageous for the acquisition, and possibly to attach necessary coils. Naturally, Steps S1 and S2 can also be implemented in a modified order.

According to the prior art, it is furthermore possible to have the following necessary measures for basic configuration of the magnetic resonance system be conducted automatically. For example, it has been long known to improve the magnetic field homogeneity of the basic magnetic field $B_0$ upon insertion of a patient wholly automatically by a technique known as "shimming" without action by the user. The damping of the radio-frequency pulses that is necessary for the measurement can also be determined automatically. Furthermore, it is known to detect the position and orientation of the patient in the magnetic resonance system automatically from automatically acquired positioning image data sets. The control device thus possesses a certain prior knowledge, as a result of which it is enabled to conduct a data acquisition by the specification of only three primary control parameters. For this, as Step S3 the user inputs the desired contrast response in input field 5, the orientation in input field 6 and the examination organ in input field 7. After the production of the automatic settings (S4) that thereupon ensues, the data acquisition can follow in Step S5. Described in more detail, and naturally known to the man skilled in the art, it is thereby that—after setting the primary parameters—the secondary parameters to control the components of the magnetic resonance system 1 can be calculated immediately (although this is not mandatory). At least a one-time shimming, a pulse angle determination and a pulse damping (thus adjustment definitions) are to be conducted. This can ensue automatically as described in Step S4. Only after this are all boundary conditions known in order to essentially calculate from these in an automated manner the time duration, gradient strengths and pulse dampings required to control the components. The calculation of these secondary control parameters thereby ensues fully automatically and hidden from the user, which is why the user need merely input the three primary control parameters.

Steps S3-S5 for automatic calculation of the control parameters are thereby conducted arbitrarily often with arbitrary examination organs and arbitrary contrasts. However, the implementation of Step S4 is thereby necessary only given variation of the patient positioning or variation of the examination organ (for example from knee to ankle). The variation of the examination organ namely mandates a movement of the patient bed in order to move the examination organ into the isocenter of the magnetic resonance system 1. The influence of the patient or of the examination subject on the magnetic field hereby changes, which is why the shimming and the determination of the pulse damping are to be repeated, for example.

After acquisition of all required measurement data, in a last Step S6 either the patient can be changed in order to thereupon begin again at Step S2, or a complete end of the measurement can also ensue. Thus only six simple steps are required by the method according to the invention for a complete data acquisition.

FIG. 4 shows a modification of the depiction in the display device 3 in which the selection field 9 for the selection of a movement-compensated measurement and a triggering of the measurement sequence in selection field 10 can be selected as additional selection fields. The selection fields 9 and 10 thereby allow a manner of quick selection of frequently required and easily understandable secondary control parameters. For example, via the selection of a movement compensation a switch can be made from a RARE sequence to a BLADE sequence that is insensitive to movement artifacts. However, the experienced user can naturally open the input fields for the secondary parameters (in which a preferred sequence can then also be directly set) via actuation of the selection field 8. The setting of the triggering can on the one hand be set automatically with the examination organ; for example, a triggering is practically always required at the heart, but there are also examination organs for which the setting of this parameter is not clearly established. Additional control parameters can naturally also be displayed on this first panel, but their use by the method according to the invention is unnecessary.

It should be noted that a prior knowledge of the examination subject is naturally required to calculate the parameters to achieve a $T_1$ weighting, for example. For example, an optimal $T_1$ contrast can only be calculated when the $T_1$ relaxation times of the tissue imaged in the images are known. Such a contrast can be optimized only between two and a non-excessive number of tissues. This is not a problem since the relaxation times and other parameters are already known from many publications, and their measurement is more or less trivial. Therefore the relaxation times to be used are also already implicitly provided with the setting of the examination organ.

The method according to the invention thus allows a significantly simplified operation of a magnetic resonance system and supervision with a minimum of prior knowledge.

Although modifications and changes may be suggested by those skilled in the art, it is the intention of the inventor to embody within the patent warranted hereon all changes and modifications as reasonably and properly come within the scope of her contribution to the art.

I claim:

1. A method for operating a magnetic resonance system comprising the steps of:
   in a control device that operates a magnetic resonance system to acquire image data from an examination subject representing a diagnostic image of the subject having an image content that allows a medical diagnosis of the examination subject to be made directly therefrom;, manually entering only three first control parameters that define first boundary conditions selected by an operator making the entry, for acquisition of said image data representing said diagnostic image, said first control parameters consisting of
      a) contrast response,
      b) spatial orientation of at least one image data set to be acquired representing a diagnostic image of the subject having an image content that allows a medical diagnosis of the examination subject to be made directly therefrom, and
      c) an organ of the patient from which said image data set is to be acquired; and
   in a processor in said control unit, automatically determining a plurality of additional, second control parameters that are necessary in order to control operation of said magnetic resonance system configured to acquire said image data, and defining second boundary conditions, using only said first control parameters, and making said second control parameters electronically available at an output of the processor in a form that is useable in operating said magnetic resonance system and in acquiring said image data representing said diagnostic image.

2. A method as claimed in claim 1 comprising entering, as said contrast response, T1 contrast, T2 contrast, diffusion contrast, perfusion contrast, magnetization transfer contrast, proton density weighting, spin density weighting, contrast quantification, and fat saturation contrast.

3. A method as claimed in claim 1 comprising entering, as said spatial orientation, an orientation selected from the group consisting of sagittal orientation, coronal orientation, transverse orientation, double oblique orientation, and in-plane rotated orientation.

4. A method as claimed in claim 1 comprising entering, as said organ, any localizable body region of the patient.

5. A method as claimed in claim 1 comprising making said second control parameters available at an output of said processor of said control unit in a humanly perceptible form, and allowing manual modification of said second control parameters, individually or in groups, in order to define values that deviate from values of said second control parameters automatically set by said processor of said control device.

6. A method as claimed in claim 1 comprising electronically storing said first control parameters and said second control parameters associated with a personalized designation of said operator.

7. A method as claimed in claim 1 comprising, from said control device, operating said magnetic resonance system, before acquiring said image data representing said diagnostic image of the subject, to acquire at least one non-diagnostic positioning image data set, and providing said at least one non-diagnostic positioning image data set to said processor and, in said processor, automatically determining said plurality of additional, second control parameters using said first control parameters and said at least one non-diagnostic positioning image data set.

8. A magnetic resonance apparatus comprising:
a magnetic resonance data acquisition unit that interacts with an examination subject;
a control device that operates said magnetic resonance data acquisition unit in order to acquire image data from the examination subject representing a diagnostic image of the subject having an image content that allows a medical diagnosis of the examination subject to be made directly therefrom;
a user interface configured to enter only three first control parameters that define first boundary conditions selected by an operator making the entry, which sets up the acquisition of said image data representing said diagnostic image, said first control parameters consisting of:
a) contrast response,
b) spatial orientation of at least one image data set to be acquired representing a diagnostic image of the subject having an image content that allows a medical diagnosis of the examination subject to be made directly therefrom, and
c) an organ of the patient from which said image data set is to be acquired; and
said control unit comprising a processor configured to automatically determine a plurality of additional, second control parameters that are necessary in order to control operation of said magnetic resonance system that is configured to acquire said image data, and define the second boundary conditions, using said first control parameters, and making said second control parameters electronically available at an output of the processor in a form that is useable in operating said magnetic resonance system and in acquiring said image data representing said diagnostic image.

9. An apparatus as claimed in claim 8 wherein said user interface is configured to enter, as said contrast response, T1 contrast, T2 contrast, diffusion contrast, perfusion contrast, magnetization transfer contrast, proton density weighting, spin density weighting, contrast quantification, and fat saturation contrast.

10. An apparatus as claimed in claim 8 wherein said user interface is configured to enter, as said spatial orientation, an orientation selected from the group consisting of sagittal orientation, coronal orientation, transverse orientation, double oblique orientation, and in-plane rotated orientation.

11. An apparatus as claimed in claim 8 wherein said user interface is configured to enter, as said organ, any localizable body region of the patient.

12. An apparatus as claimed in claim 8 comprising a display at which said control unit makes said second control parameters available in a humanly perceptible form, and wherein said user interface is configured in order to allow manual modification of said second control parameters, individually or in groups, to defined values that deviate from values of said second control parameters automatically set by said processor of said control device.

13. An apparatus as claimed in claim 8 comprising a memory in which said first control parameters and said second control parameters are stored associated with a personalized designation of said operator.

14. An apparatus as claimed in claim 8 wherein said control device is configured to operate said magnetic resonance data acquisition unit, prior to acquiring said image data representing said diagnostic image of the subject, to acquire at least one non-diagnostic positioning image data set, said at least one non-diagnostic image data set being supplied to said processor, and said processor being configured to automatically determine said plurality of additional, second control parameters using said first control parameters and said at least one non- diagnostic positioning image data set.

* * * * *